United States Patent
Souvie et al.

(10) Patent No.: US 7,196,204 B2
(45) Date of Patent: Mar. 27, 2007

(54) METHOD FOR THE SYNTHESIS OF S-INDOLINE-2-CARBOXYLIC ACID AND APPLICATION THEREOF IN THE SYNTHESIS OF PERINDOPRIL

(75) Inventors: Jean-Claude Souvie, Le Havre (FR); Jean-Pierre Lecouve, Le Havre (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/552,676

(22) PCT Filed: Apr. 7, 2004

(86) PCT No.: PCT/FR2004/000857

§ 371 (c)(1),
(2), (4) Date: Oct. 7, 2005

(87) PCT Pub. No.: WO2004/092095

PCT Pub. Date: Oct. 28, 2004

(65) Prior Publication Data

US 2006/0183919 A1    Aug. 17, 2006

(30) Foreign Application Priority Data

Apr. 9, 2003 (EP) .................................. 03290879

(51) Int. Cl.
C07D 209/12 (2006.01)

(52) U.S. Cl. ...................................... 548/493; 548/452

(58) Field of Classification Search ................ 548/452, 548/493
See application file for complete search history.

(56) References Cited

U.S. PATENT DOCUMENTS

| 4,914,214 A | * | 4/1990 | Vincent et al. ............. 548/492 |
| 5,220,053 A | | 6/1993 | Choudhury et al. |

FOREIGN PATENT DOCUMENTS

| DE | 3727 411 | 3/1988 |
| EP | 0468 592 | 1/1992 |
| EP | 0308341 | 3/1998 |

OTHER PUBLICATIONS

International Search Report: PCT FR 2004 000857: Sep. 23, 2004.
International Preliminary Examination Report: PCT FR 2004 000857 Jul. 21, 2005.

* cited by examiner

*Primary Examiner*—Joseph K. McKane
*Assistant Examiner*—Michael P. Barker
(74) *Attorney, Agent, or Firm*—Hueschen and Sage

(57) ABSTRACT

Process for the synthesis of (2S)-indoline-2-carboxylic acid of formula (I):

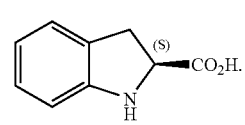

Application in the synthesis of perindopril and its pharmaceutically acceptable salts.

4 Claims, No Drawings

METHOD FOR THE SYNTHESIS OF S-INDOLINE-2-CARBOXYLIC ACID AND APPLICATION THEREOF IN THE SYNTHESIS OF PERINDOPRIL

The present invention relates to a process for the synthesis of (2S)-indoline-2-carboxylic acid, and to its application in the synthesis of perindopril and pharmaceutically acceptable salts thereof.

More specifically, the present invention relates to a new process for the industrial synthesis of (2S)-indoline-2-carboxylic acid of formula (I):

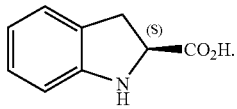

The compound of formula (I) obtained according to the process of the invention is useful in the synthesis of perindopril of formula (II):

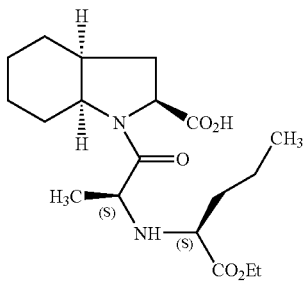

and in the synthesis of pharmaceutically acceptable salts thereof.

Perindopril and salts thereof have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European patent specification EP 0 049 658.

In view of the pharmaceutical value of this compound, it has been important to be able to obtain the intermediate of formula (I) by an effective synthesis process that allows the (S) enantiomer to be obtained selectively in a very good yield and with excellent purity.

Some methods for the preparation of the compound of formula (I) are already known.

Thus, the patent specifications EP 0 308 339 and EP 0 308 341 describe obtaining (2S)-indoline-2-carboxylic acid by resolution of racemic indoline-2-carboxylic acid using (R)-α-methylbenzylamine. The (R)-α-methylbenzylamine salt of (2S)-indoline-2-carboxylic acid is isolated by fractional crystallisation, then acidified to yield the compound of formula (I).

That method has the advantage of using a starting material and reagents that are reasonably priced and very readily accessible.

On the other hand, the yield of the compound of formula (I) using that method is only 35%.

The Applicant has now developed a process for the synthesis of the compound of formula (I) in which the (2R) isomer, which is formed during the course of the resolution reaction, is recycled. The process developed in that way makes it possible to obtain the compound of formula (I) in a yield, starting from racemic indoline-2-carboxylic acid, that ranges from 50% to 70%, according to the number of recycling operations carried out.

More specifically, the present invention relates to a process for the synthesis of the compound of formula (I) which is characterised in that racemic indoline-2-carboxylic acid of formula (III):

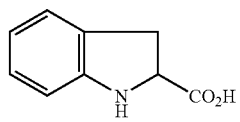

is reacted with a chiral amine
to yield the salt of formula (IV):

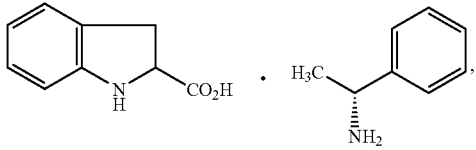

which is filtered off, and there being isolated:
on the one hand the (2S) isomer of formula (IV a):

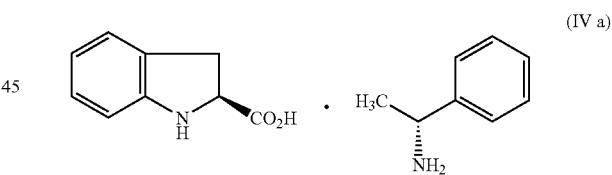

in the form of crystals,
which compound of formula (IV a) is then treated with hydrochloric acid to yield the compound of formula (I),
and on the other hand a mixture of the (2S) isomer of formula (IV a) and the (2R) isomer of formula (IV b) in which the (2R) isomer predominates:

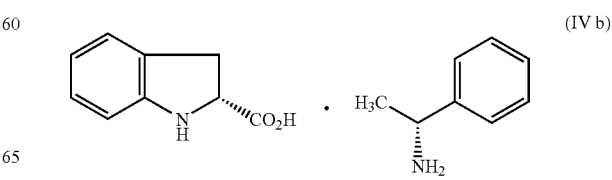

by evaporation of the filtrate,
which mixture is then treated with hydrochloric acid to yield a mixture of (2R)-indoline-2-carboxylic acid and (2S)-indoline-2-carboxylic acid in which the (2R) acid predominates,
which is racemised by reaction with sodium hydroxide solution,
at a temperature of from 140 to 200° C.,
under a pressure of from 5 to 15 bars,
to yield, after isolation, the compound of formula (III), with which the series of operations described above is repeated, then, after having carried out from 2 to 6 cycles, all the portions made up of the compound of formula (I) are combined.

The compound of formula (I) is thereby obtained in a yield ranging from 50% to 70%, according to the number of cycles carried out.

Its chemical and enantiomeric purity is very good, which makes its use in the synthesis of perindopril of formula (II) especially advantageous.

By way of illustration, the catalytic hydrogenation of the compound of formula (I) obtained according to the process of the invention, followed by coupling of the (2S,3aS,7aS)-perhydroindole-2-carboxylic acid so obtained with the compound of formula (VI):

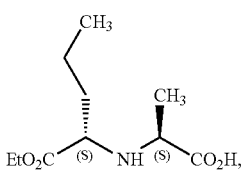

allows perindopril of formula (II) to be obtained in very satisfactory purity and yield.

The present invention relates also to a variant of the above process in which there is reacted (2R)-indoline-2-carboxylic acid of formula (V):

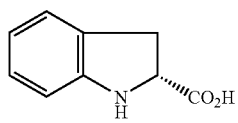

which is racemised by reaction with sodium hydroxide solution,
at a temperature of from 140 to 200° C.,
under a pressure of from 5 to 15 bars,
to yield, after isolation, the compound of formula (III):

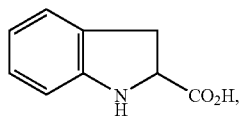

which is reacted with a chiral amine
to yield the salt of formula (IV):

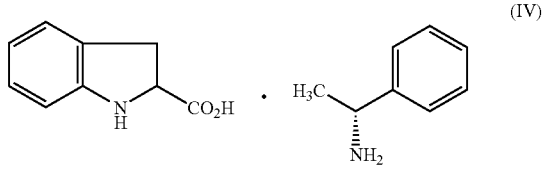

which is filtered off, and there being isolated:
on the one hand the (2S) isomer of formula (IV a):

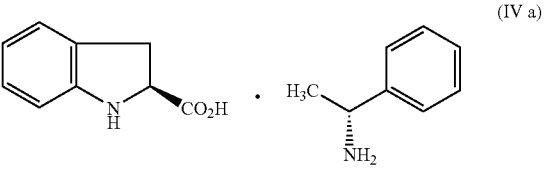

in the form of crystals,
which compound of formula (IV a) is then treated with hydrochloric acid to yield the compound of formula (I),
and on the other hand a mixture of the (2S) isomer of formula (IV a) and the (2R) isomer of formula (IV b) in which the (2R) isomer predominates:

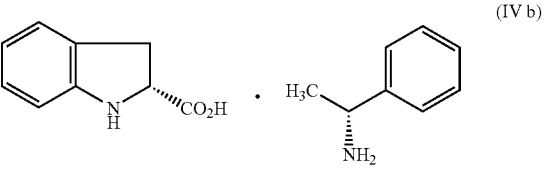

by evaporation of the filtrate,
which mixture is then treated with hydrochloric acid to yield a mixture of (2R)-indoline-2-carboxylic acid and (2S)-indoline-2-carboxylic acid in which the (2R) acid predominates,
with which there is repeated, if desired, the series of operations described above,
then, after having carried out from 1 to 6 cycles, all the portions made up of the compound of formula (1) are combined.

Among the chiral amines that can be used in the process according to the invention or its variant there may be mentioned, without implying any limitation, (R)-α-methyl-benzyl-amine, 1-(1-naphthyl)-ethylamine, ephedrine, α-chymotrypsin, sec-butylamine, 1-amino-2-methylbutane, N,N-dimethyl-1-phenylethylamine, 1-cyclohexylethylamine, cycloserine, 2-(methoxymethyl)-pyrrolidine, α-dimethylamino-ε-caprolactam, isobornylamine, 1-(4-nitrophenyl)-ethylamine, α-amino-ε-caprolactam, 2-amino-1-butanol, 1-amino-2-propanol, cinchonidine, cinchonine, N-methyl-ephedrine, phenylalaninol, quinidine, valinol, α-phenyl-glycinol, leucinol.

The preferred chiral amine is (R)-α-methylbenzylamine.

"Mixture in which (2R) predominates" is understood to mean a mixture of (2R) and (2S) isomers in which the (2R) isomer forms the majority of the mixture.

The Example below illustrates the invention.

EXAMPLE (2S)-indoline-2-carboylic acid

Step A: Resolution of Racemic indoline-2-carboxylic acid 3.7 kg of (R)-α-methylbenzylamine are added to a solution of 5 kg of indoline-2-carboxylic acid in ethanol and then the mixture is stirred for 2 h and filtered.

Step $A_1$: (2S)-indoline-2-carboxylic acid

The white precipitate collected in Step A is recrystallised from isopropanol and then dissolved in 13 liters of water, and 12 liters of a 1N hydrochloric acid solution are added. After stirring for 2 h, the precipitate is filtered off and then washed and dried to yield (2S)-indoline-2-carboxylic acid («$1^{st}$ portion») in the form of crystals (1.80 kg) with a chemical purity of 98% and an enantiomeric purity greater than 99.5%.

Step $A_2$: Idoline-2-carboxylic acid (Mixture in Which (2R) Predominates)

The filtrate collected in Step A is evaporated and the residue obtained is dissolved in 13 liters of water and then 12 liters of a 1 N hydrochloric acid solution are added. After stirring for 2 h, the precipitate is filtered off and then washed and dried to yield indoline-2-carboxylic acid in the form of a mixture of the (2R) and (2S) enantiomers (2.6 kg) in which the (2R) enantiomer predominates.

Step B: Racemisation

Introduce into an autoclave the precipitate obtained in Step $A_2$ (2.6 kg), and then 12 liters of water and 3.1 liters of an 8.65N sodium hydroxide solution, then heat at 170° C. for 3 h under a pressure of 7 bars.

The reaction mixture is subsequently brought to ambient temperature and then transferred to a reactor, and concentrated hydrochloric acid is subsequently added until a pH of 3.4 is reached while maintaining the temperature between 20 and 25° C.

The mixture is then stirred for 1 h and the precipitate is subsequently filtered off, washed and dried to yield racemic indoline-2-carboxylic acid in a yield of 90% (2.34 kg).

Step C: Recycling of indoline-2-carboxylic Acid

The racemic indoline-2-carboxylic acid obtained in Step B (2.34 kg) is resolved according to the procedure in Step A.

The (R)-α-methylbenzylamine salt of (2S)-indoline-2-carboxylic acid so formed is isolated and then treated with hydrochloric acid according to the procedure in Step $A_1$ to yield (2S)-indoline-2-carboxylic acid («$2^{nd}$ portion») in the form of crystals (0.84 kg) having a chemical purity of 98% and an enantiomeric purity greater than 99.5%.

The $1^{st}$ portion, obtained in Step $A_1$, and the $2^{nd}$ portion, obtained in Step C, are then combined.

(2S)-indoline-2-carboxylic acid is thereby obtained in a total yield of 52.8%, a chemical purity of 98% and an enantiomeric purity greater than 99.5%.

The invention claimed is:

1. A process for the synthesis of (2S)-indoline-2-carboxylic acid of formula (I):

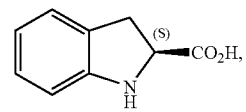

(I)

wherein a racemic indoline-2-carboxylic acid of formula (III):

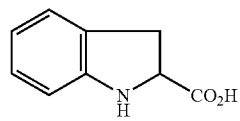

(III)

is reacted with a chiral amine
to yield a salt of formula (IV):

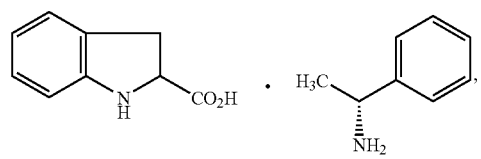

(IV)

which is filtered off, to yield:
the (2S) isomer of formula (IV a):

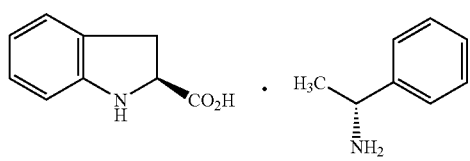

(IV a)

in the form of crystals,
which compound of formula (IV a) is treated with hydrochloric acid to yield the compound of formula (I),
and after evaporation of the filtrate, a mixture of the (2S) isomer of formula (IV a) and the (2R) isomer of formula (IV b) in which the (2R) isomer predominates:

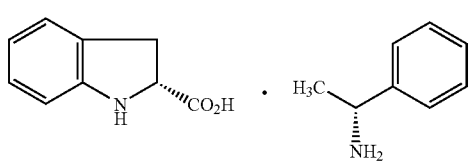

(IV b)

which mixture is treated with hydrochloric acid to yield a mixture of (2R)-indoline-2-carboxylic acid and (2S)-indoline-2-carboxylic acid in which the (2R) acid predominates, the mixture is racemized by reaction with a sodium hydroxide solution, at a temperature of from 140 to 200° C., under a pressure of from 5 to 15 bars, to yield, after isolation, the compound of formula (III), which is then re-subjected to the series of operations described above, after having carried out between 2 and 6 cycles of the above-described series of operations, all the portions made up of the compound of formula (I) are combined.

2. A process for the synthesis of (2S)-indoline-2-carboxylic acid of formula (I):

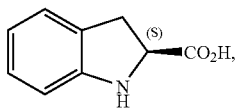

(I)

wherein (2R)-indoline-2-carboxylic acid of formula (V):

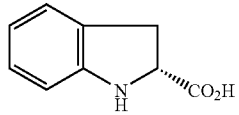

(V)

is racemized by reaction with a sodium hydroxide solution, at a temperature of from 140 to 200° C., under a pressure of from 5 to 15 bars, to yield, after isolation, a compound of formula (III):

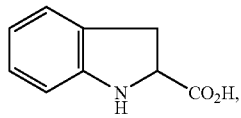

(III)

which is reacted with a chiral amine, to yield a salt of formula (IV):

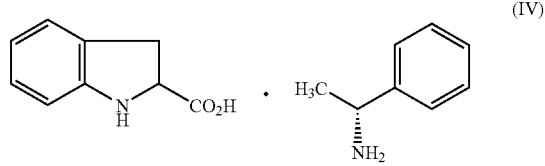

(IV)

which is filtered off, to yield:
the (2S) isomer of formula (IV a):

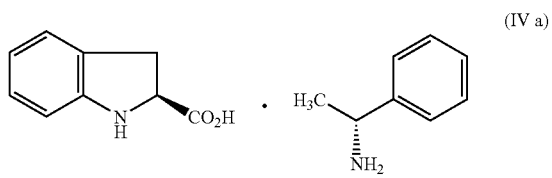

(IV a)

in the form of crystals,
which compound of formula (IV a) is treated with hydrochloric acid to yield the compound of formula (I),
and, after evaporation of the filtrate, a mixture of the (2S) isomer of formula (IV a) and the (2R) isomer of formula (IV b) in which the (2R) isomer predominates:

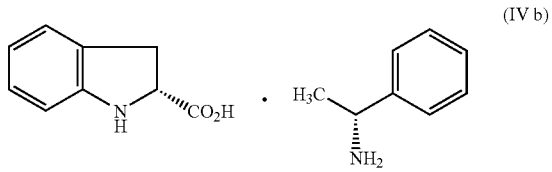

(IV b)

which mixture is treated with hydrochloric acid to yield a mixture of (2R)-indoline-2-carboxylic acid and (2S)-indoline-2-carboxylic acid in which the (2R) acid predominates, the mixture is re-subjected, if desired, to the series of operations described above, after having carried out from 1 to 6 cycles of the above-described series of operations, all the portions made up of the compound of formula (I) are combined.

3. A process according to claim 1, wherein the chiral amine is (R)-α-methylbenzylamine.

4. A process according to claim 2, wherein the chiral amine is (R)-α-methylbenzylamine.

* * * * *